United States Patent
Roberts

(10) Patent No.: US 9,770,609 B2
(45) Date of Patent: Sep. 26, 2017

(54) UREA BASED SKIN TREATMENT

(71) Applicant: Neat Feat Products Limited, Auckland (NZ)

(72) Inventor: David Ian Roberts, Bald Hills (AU)

(73) Assignee: Neat Feat Products Limited, Auckland (NZ)

( * ) Notice: Subject to any disclaimer, the term of this patent is extended or adjusted under 35 U.S.C. 154(b) by 0 days.

(21) Appl. No.: 14/676,027

(22) Filed: Apr. 1, 2015

(65) Prior Publication Data

US 2016/0287498 A1    Oct. 6, 2016

(51) Int. Cl.
| | | |
|---|---|---|
| *A61K 8/40* | (2006.01) | |
| *A61Q 19/00* | (2006.01) | |
| *A61K 8/87* | (2006.01) | |
| *A61K 8/34* | (2006.01) | |
| *A61K 8/42* | (2006.01) | |

(52) U.S. Cl.
CPC ............ *A61Q 19/007* (2013.01); *A61K 8/345* (2013.01); *A61K 8/42* (2013.01); *A61K 8/87* (2013.01)

(58) Field of Classification Search
CPC .......... A61Q 19/007; A61K 8/40; A61K 8/87; A61K 8/345
See application file for complete search history.

(56) References Cited

U.S. PATENT DOCUMENTS

| | | | |
|---|---|---|---|
| 4,690,815 A | 9/1987 | Deckner | |
| 8,865,143 B2 * | 10/2014 | Lu | A01N 25/00 424/63 |
| 2003/0012749 A1 | 1/2003 | Kraemer et al. | |
| 2003/0044364 A1 | 3/2003 | Meyer et al. | |
| 2004/0146555 A1 | 7/2004 | Ulbricht et al. | |
| 2005/0037040 A1 | 2/2005 | Arkin et al. | |
| 2007/0258935 A1 | 11/2007 | McEntire et al. | |
| 2008/0247976 A1 | 10/2008 | Dueva-Koganov et al. | |
| 2013/0177504 A1 * | 7/2013 | Macoviak | A61K 8/29 424/10.3 |

FOREIGN PATENT DOCUMENTS

| | | |
|---|---|---|
| EP | 1 293 204 A1 | 3/2003 |
| EP | 2 153 814 A1 | 2/2010 |
| GB | 2496656 A | 5/2013 |
| WO | 00/10523 A1 | 3/2000 |
| WO | 00/48568 A1 | 8/2000 |
| WO | 01/00163 A1 | 1/2001 |

OTHER PUBLICATIONS

Lubrizol, title: Formulating Tips for Avalure™ Polymers, published Nov. 1, 2012.*
Database GNPD, Mintel, May 2014, "Cracked heel extra plus repair", XP002752548, total of 3 pages.
"Avalure™ Film-Forming Polymers for Personal Care Applications." Lubrizol, Technical Data Sheet, Mar. 4, 2011, http://www.personalcare.noveon.com/TechnicalDataSheets/tds248.pdf, total of 3 pages.

* cited by examiner

*Primary Examiner* — Yanzhi Zhang
(74) *Attorney, Agent, or Firm* — Collard & Roe, P.C.

(57) ABSTRACT

A topical formulation for treating human skin, having:
urea;
to film forming polymer;
humectant;
preservative; and
water
the above ingredients being combined such that the preservative protects the formulation against bacterial invasion, the humectant assists the formulation to retain water, and the water and film forming polymer enable the urea to be applied to human skin such that the urea sits on the skin as a stable film and is gradually absorbed into the skin to alleviate dryness or cracking.

9 Claims, No Drawings

UREA BASED SKIN TREATMENT

FIELD OF INVENTION

A preferred form of this invention relates to a urea based treatment for human skin, particularly for one's feet, and especially, but not necessarily, the heels.

BACKGROUND

Many people suffer from dry skin at their feet. In some cases the skin may flake off or crack. It is known to apply urea based heel balms to the feet as it is thought this helps the skin to retain a healthy amount of water. Some known products rely on heavy oily emulsions to get the urea into the skin, but a downside is that they can be messy and may cause staining of bed linen, etc. They can also make the feet undesirably slippery, which may present a safety risk. It is an object of a preferred embodiment of the invention to go at least some way towards addressing at least some of these shortcomings. While this object applies to the preferred embodiment, it should be understood that the object of the invention per se is simply to provide the public with a useful choice. Therefore any objects applicable to the preferred embodiment should not be taken as a limitation on the scope of the claims to protection set out later in this document.

The term "comprises" or derivatives of this should not be interpreted as limiting. For example if used in relation to a combination of features it should be taken to indicate that optionally, but not necessarily, there may be additional features that have not been mentioned.

SUMMARY OF INVENTION

According to one aspect of the invention there is provided a topical formulation for treating human skin, having:
urea;
film forming polymer;
humectant;
preservative; and
water
the above ingredients being combined such that the preservative protects the formulation against bacterial invasion, the humectant assists the formulation to retain water, and the water and film forming polymer enable the urea to be applied to human skin such that the urea sits on the skin as a stable film and is gradually absorbed into the skin to alleviate dryness or cracking.

Optionally the formulation has 25%-35% urea, by weight.

Optionally the formulation has about 30% urea, by weight.

Optionally the film forming polymer comprises a urethane polymer.

Optionally the film forming polymer comprises PPG-17/IPDI/DMPA copolymer.

Optionally the humectant comprises glycerine.

Optionally the preservative comprises one or more of phenoxyethanol, methyl paraben, ethyl paraben, propyl paraben and butyl paraben, and preferably a combination of all of these.

Optionally the preservative comprises *Salichem* preservative or *Phenonip* preservative.

According to a broader aspect of the invention, there is provided topical formulation for treating human skin, having:
urea;
film forming polymer; and
water
the above ingredients being combined such that the water and film forming polymer enable the urea to be applied to human skin such that the urea sits on the skin as a stable film and is gradually absorbed into the skin to alleviate dryness or cracking.

DETAILED DESCRIPTION

According to a preferred embodiment of the invention a topical formulation for heel skin is prepared from a mixture of the following ingredients:

| Ingredient | Amount (grams) | Function |
| --- | --- | --- |
| Urea | 300 | therapeutic agent |
| water | 603 | Solvent |
| Avalure 450 polymer (PPG-17/IPDI/DMPA copolymer) | 45 | Film forming polymer |
| Glycerine | 50 | humectant |
| *Salichem* preservative or *Phenonip* preservative | 2 | preservative |

It had not previously been known to formulate urea with a film forming polymer and, when done, the inventor found that it gave surprisingly good results.

The formulation is preferably prepared according to the following procedure—
a) obtain 603 gm of water at room temperature;
b) slowly add 300 gm of urea to the water, with constant stirring, until completely dissolved;
c) slowly add 45 gm of Avalure 450 (PPG-17/IPDI/DMPA—chemical name polyoxypropylene(17) isophorone diisocyanate and dimethylol propionic acid copolymer provided by The Lubrizol Corporation) film forming polymer to the mix, with constant stirring, until a milky white homogeneous solution is achieved;
d) add 50 gm of glycerine to the mix, with constant stirring, until dissolved;
e) add 2 gm of a preservative to the mix (eg phenoxyethanol, methyl paraben, ethyl paraben, propyl paraben and butyl paraben), with constant stirring, until dissolved; and
f) continue mixing until a milky-white solution free of particles is achieved.

When created, the formulation is substantially waterproof (ie will not readily wash off the skin), is non-staining and does not have the sort of greasy or oily consistency of many prior art formulations.

As indicated in the table, the urea is preferably at an amount of 30% by weight. However in other embodiments of the invention there may be more, or less. For example the urea may be at 25-35% by weight.

As well as providing humectant functionality, the glycerine assists in making the formulation smooth. It imparts lubricant type characteristics.

It will be appreciated that alternative film forming polymers, humectants and preservatives may be used in place of those specifically mentioned above. However in each case the film forming polymer will be sufficient to give a stable urea containing film when applied to a human topically, and at least much of the urea able to be readily absorbed into the skin. Preferably the formulation is a spray-on one and is delivered by way of a spray dispenser.

While some preferred forms of the invention have been described by way of example, it should be understood that modifications and improvements can occur without departing from the scope of the following claims.

The invention claimed is:

1. A topical formulation for treating human skin, having 25% to 35% urea by weight based on the total weight of the topical formulation; film forming polymer; a humectant; a preservative; and water, wherein the urea having a molecular formula $H_2NCONH_2$; wherein the film forming polymer comprises polyoxypropylene(17) isophorone diisocyanate and dimethylol propionic acid copolymer (PPG-17/IPDI/DMPA copolymer), the above ingredients being combined such that the preservative protects the formulation against bacterial invasion, the humectant assists the formulation to retain water, and the water and film forming polymer enable the urea to be applied to human skin such that the urea sits on the skin as a stable film and is gradually absorbed into the skin to alleviate dryness or cracking, the film being waterproof.

2. A formulation according to claim 1, having about 30% urea, by weight based on the total weight of the topical formulation.

3. A formulation according to claim 1, having 30% urea, by weight based on the total weight of the topical formulation.

4. A formulation according to claim 1, wherein the humectant comprises glycerine.

5. A formulation according to claim 1, wherein the preservative comprises one or more phenoxyethanol, methyl paraben, ethyl paraben, propyl paraben and butyl paraben, and preferably a combination of these.

6. A formulation according to any one of claim 1, wherein the preservative comprises phenoxyethanol, methyl paraben, ethyl paraben, propyl paraben and butyl paraben preservative or phenoxyethanol, methyl paraben, ethyl paraben, propyl paraben and butyl paraben and isobutyl paraben preservative.

7. A formulation according to claim 1, wherein the film forming polymer comprises a polyurethane substance and the humectant comprises glycerine.

8. A formulation according to claim 6, wherein the urea is in an amount of approximately 30% by weight.

9. A topical formulation for treating human skin, having 25% to 35% urea by weight based on total weight of the topical formulation; film forming polymer; and water, wherein the urea having a molecular formula $H_2NCONH_2$; wherein the film forming polymer comprises polyoxypropylene(17) isophorone diisocyanate and dimethylol propionic acid copolymer (PPG-17/IPDI/DMPA copolymer), the above ingredients being combined such that the water and film forming polymer enable the urea to be applied to human skin such that the urea sits on the skin as a stable film and is gradually absorbed into the skin to alleviate dryness or cracking; the film being waterproof.

* * * * *